(12) United States Patent
Van Workum et al.

(10) Patent No.: US 12,290,809 B2
(45) Date of Patent: May 6, 2025

(54) SAMPLE MANAGEMENT MODULE

(71) Applicant: Panacea Diagnostics LTD, London (GB)

(72) Inventors: Stefan Leo Van Workum, London (GB); Callum Robertson Smith, London (GB); Marko Dorrestijn, London (GB); David R. Klug, London (GB)

(73) Assignee: Panacea Diagnostics Ltd, London (GB)

( * ) Notice: Subject to any disclaimer, the term of this patent is extended or adjusted under 35 U.S.C. 154(b) by 287 days.

(21) Appl. No.: 17/435,373

(22) PCT Filed: Feb. 28, 2020

(86) PCT No.: PCT/GB2020/050485
§ 371 (c)(1),
(2) Date: Aug. 31, 2021

(87) PCT Pub. No.: WO2020/178563
PCT Pub. Date: Sep. 10, 2020

(65) Prior Publication Data
US 2022/0143608 A1 May 12, 2022

(30) Foreign Application Priority Data
Mar. 1, 2019 (GB) ..................... 1902792

(51) Int. Cl.
*B01L 3/00* (2006.01)
*A61B 10/00* (2006.01)

(52) U.S. Cl.
CPC .... *B01L 3/502715* (2013.01); *A61B 10/0051* (2013.01); *B01L 3/5023* (2013.01);
(Continued)

(58) Field of Classification Search
CPC ............ B01L 3/502715; B01L 3/5023; B01L 2200/0684; B01L 2300/041;
(Continued)

(56) References Cited

U.S. PATENT DOCUMENTS

2002/0004019 A1  1/2002  Bachand et al.
2004/0248316 A1  12/2004  Percival et al.
(Continued)

FOREIGN PATENT DOCUMENTS

EP   2 050 498 A1   4/2009
EP   2 777 499 A1   9/2014
(Continued)

OTHER PUBLICATIONS

International Search Report and Written Opinion for International Application No. PCT/GB2020/050485 mailed Aug. 25, 2020.
(Continued)

*Primary Examiner* — Samuel P Siefke
(74) *Attorney, Agent, or Firm* — Maine Cernota & Curran

(57) ABSTRACT

A sample management module for collecting a fluid sample is provided. The module comprising; a sample collection device comprising a sample collection location; a decoupling zone configured to receive sample from the collection device, an overflow reservoir in fluid communication with the decoupling zone to accommodate any sample that does not fit into the decoupling zone; wherein the overflow reservoir is configured to ensure pressure within the module can be managed. A cartridge comprising a sample management module is also provided.

14 Claims, 10 Drawing Sheets

(52) U.S. Cl.
CPC .............. *A61B 2010/0006* (2013.01); *B01L 2200/0684* (2013.01); *B01L 2300/041* (2013.01); *B01L 2300/161* (2013.01)

(58) Field of Classification Search
CPC ......... B01L 2300/161; B01L 2200/026; B01L 2300/043; B01L 2300/0681; B01L 2300/069; B01L 2400/0406; B01L 2400/0694; B01L 3/502753; B01L 3/502723; B01L 2300/023; B01L 2300/024; B01L 2300/025; B01L 2300/14; B01L 2400/0481; A61B 10/0051; A61B 2010/0006
See application file for complete search history.

(56) References Cited

U.S. PATENT DOCUMENTS

2011/0171754 A1    7/2011  Redmond et al.
2017/0059551 A1*   3/2017  Patwardhan ........... B01D 63/08

FOREIGN PATENT DOCUMENTS

| WO | 2013/064558 A1 | 5/2013 |
| WO | WO 2014/179215 A1 | 11/2014 |
| WO | WO 2018/163109 A1 | 9/2018 |

OTHER PUBLICATIONS

Combined Search and Examination Report under Sections 17 and 18(3) for GB Application No. GB1902792.9 dated Aug. 27, 2019.

\* cited by examiner

SAMPLE MANAGEMENT MODULE

RELATED APPLICATIONS

This Application is a national stage filing under 35 U.S.C. 371 of International Patent Application Serial No. PCT/GB2020/050485, filed Feb. 28, 2020, entitled "IMPROVEMENTS IN OR RELATING TO A SAMPLE MANAGEMENT MODULE," which claims priority to GB application number GB 1902792.9, filed Mar. 1, 2019, each of which is incorporated herein by reference in its entirety.

The present invention relates to improvements in or relating to a sample management module and in particular, a sample management module for collecting a fluid sample.

A point-of-care diagnostic system often includes a disposable cartridge and a reader. The cartridge can be inserted into the reader and the sample such as a blood, saliva or urine can be analysed. Bioassays are often performed on a device such as an assay cartridge in order to detect certain biomarkers within a sample which is within the cartridge.

In order to identify the presence or absence of certain biomarkers in a fluid sample, a device is required to collect a fluid sample from a patient/user in an efficient manner, at the point of care. As the device is being utilised at the point of care, potentially by an unskilled operative, the device must be intuitive to use and should be resilient.

As the device may be in the hands of an unskilled operative, it is important that no fluid should leave the device, whether that is excess sample re-emerging from the device or reagents provided within the device from exiting the device.

The device also needs to interface with a reader which is configured to access data either in the form of raw data such as a measurement of luminescence or it may be a binary result indicating the presence or absence of a predetermined biomarker.

Fluid samples may contain other particles and contaminants which may interact with the bioassays and mask the action of the biomarker under review. This may result in erroneous readings. Thus, it is highly desirable to provide a collection sample device that significantly reduces or eliminate contaminants or any unwanted particles before analysis.

In addition, there is also a requirement to collect the fluid sample in an appropriate volume in order to stop excess sample leaking out of the device or getting in the user's way or contaminating the reader into which the cartridge may be inserted.

It is against this background that the present invention has arisen.

According to the present invention there is provided a sample management module for collecting a fluid sample, the module comprising; a sample collection device comprising a sample collection location; a decoupling zone configured to receive sample from the collection device, an overflow reservoir in fluid communication with the decoupling zone to accommodate any sample that does not fit into the decoupling zone; wherein the overflow reservoir configured to ensure pressure within the module can be managed.

The overflow reservoir may be configured to ensure pressure within the module can be managed via the provision of a vent. The vent manages the pressure within the module by enabling the egress of air as the sample enters the module and displaces it. The vent may be a simple opening, the size of which is selected to be sufficiently small that surface tension of the fluid sample prevents the fluid sample from flowing into the vent.

In some embodiments, the vent may comprise a permeable filter. This enables the vent to be sufficiently large that surface tension would not be sufficient to prevent the fluid sample from entering the vent, but the permeability of the filter keeps the sample in the module whilst allowing air to exit the module.

In some embodiments, the overflow reservoir itself may provide sufficient pressure regulation by virtue of its size. If a very large reservoir is provided in comparison with the size of sample expected, then the reservoir itself can manage the pressure within the module.

The provision of an overflow reservoir that is vented ensures that, even if an excess of fluid sample is collected, it cannot flow out of the device. This ensures that the sample cannot contaminate a reader or other ancillary device such as stacker or incubator into which the device may be inserted, in use. It also reassures the unskilled user that the device is effective and provides a degree of quality assurance to the user. Furthermore, partially filling the reservoir can be advantageous in that it protects the sample in the analysis zone from evaporation. There will be evaporation from the surface of the sample and therefore, if the reservoir is not at least partially filled this evaporation would occur from the sample in the decoupling or analysis zone which could have a detrimental effect on the analysis.

The decoupling, in the decoupling zone, of the loading of the sample from the analysis of the sample can ensure that the user cannot accidently impact on the analysis as the decoupling zone provides a buffer between the sample management module and the subsequent analysis of the sample.

In some embodiments, the sample collection device may further comprise a pad of material. The material may be porous such that the sample can move through the pores to exit the pad, whereas particulate contaminants will be retained in the pad. The porous nature of the pad also correlates with its compressible nature. The pad can be sized to fill the sample collection location and even have an uncompressed height that exceeds the height of the sample collection location such that, when the lid is closed, the pad is compressed. Alternatively, the pad can be a thin, single layer pad. The pores in the pad hold the sample fluid and also capture unwanted particulate contaminants so the pad can have a secondary function as a filter for larger particulate contaminants. The porous material may absorb the sample and holds the sample in the sample collection device until the lid is closed and the sample is forced from the porous material out of the sample collection location and into the decoupling zone.

In some embodiments, the pad of porous material may be passivated. Passivation of the pad of porous material may be intended to reduce binding of protein or other analytes.

In some embodiments, the pad of porous material may be removable. If the pad is removable, it can be placed in the mouth by the user and saturated with saliva. The size and absorbency of the pad will therefore dictate the size of the sample required. This removes the requirement on the user to estimate the correct sample size.

In some embodiments, the pad of porous material may be configured to provide visible indication when sample has been collected.

This provision of a positive indication that sufficient sample has been collected gives confidence to the user and also reduces the failure rate in connection with insufficient sample.

In some embodiments, the positive indication can be one or more of a colour change or a transparency change. A colour change is easily understandable to the unskilled user and makes the device user friendly. The changes may be deployed together so that the transparency of the pad changes when sufficient sample has been collected and this increase in transparency allows a coloured backing to become visible to the user. So, the user perceives a colour change, but this has been facilitated by a change in transparency the pad of porous material.

In some embodiments, the pad may be provided with a taste or smell to promote salivary excretion.

In some embodiments, the porous material can act as a filter provided upstream of the decoupling zone. The filter is provided to remove contaminants and/or unwanted particles from the sample. In some embodiments a filter can be provided where no pad is provided. In some embodiments, both the pad and the filter can be provided.

The sample management module may further comprise a lid. In some embodiments, the lid may be provided with a single use clip.

In this context a single use clip is a clip that closes once and then cannot be opened again by the user. This prevents the sample management module from being used multiple times and ensures that it is a single use item. This prevents contamination of the sample with other samples as multiple samples will never be present within the sample management module.

In some embodiments, the sample collection device may be configured to enable the sample to be drawn passively into the decoupling zone.

In some embodiments, the grooves can be provided to enable the sample to be drawn passively into the decoupling zone. The grooves may enable the sample to move via capillary action from the sample collection device into the decoupling zone.

In some embodiments, the sample collection device may be substantially circular and the grooves may be radial in the sample collection device. In some embodiments, the grooves may extend into the decoupling zone. In some embodiments, the grooves can be hydrophilic.

In a further embodiment, the configuration of the grooves enhances the hydrophilicity of the grooves. In some embodiments, the surface hydrophilicity of the grooves may additionally result from the provision of a coating to the grooves. Hydrophilic grooves make the device agnostic as to orientation so that the fluid can be drawn in even when it is upside down. The grooves may be tapered towards the decoupling zone.

In some embodiments, the lid may be configured such that the closure of the lid forces the sample from the sample collection location into the decoupling zone.

In some embodiments, the sample collection device and pad may be removable. In this embodiment, the sample collection device and pad are removed together from the sample management module. This enables the user to hold the sample collection device. This prevents contamination of the pad with particles from the fingers of the user.

In some embodiments, the lid may compress the pad to squeeze the sample out of the pad and into the decoupling zone.

In another aspect of the present invention, there is provided a cartridge comprising a sample collection module according to a previous aspect of the invention.

The cartridge may further comprise an analysis zone downstream of the sample management module. Once the sample has been collected in the sample management module it can be flowed into the analysis zone for analysis. The sample may be actively or passively flowed into the analysis zone. In embodiments where the sample is actively flowed this can be achieved through the use of a pump or a pressure differential created by the user or reader. In embodiments where the sample is passively flowed this can be achieved by capillary forces generated by the geometry of the analysis zone and the surface properties of the materials used.

The management of pressure through the cartridge is important to ensure that the flow of fluids is controlled satisfactorily. In particular, it is important that the pressure in the analysis zone does not exceed a predetermined maximum pressure of the vent hole forming the part of the flow control system that is located at the exit of the analysis zone. If this threshold pressure were to be exceeded, then additional sample would be drawn through the analysis zone and this could impact the result.

The cartridge may further comprise a pad, capillary stop or vent hole forming part of the flow control system downstream of the analysis zone. If a pad is present downstream of the analysis zone, it can absorb fluid from the analysis zone, whilst venting air from the cartridge. Presence of fluid within the pad can be taken as a positive indication that sufficient fluid has been provided for the cartridge to function effectively.

In some embodiments, the cartridge may further comprise a pressure equalisation path. The pressure equalisation path may comprise a vent from the analysis zone back through the sample management module. The provision of such an additional vent ensures that there is a closed loop for air recirculation within a close proximity of the sample collection location.

Therefore if the user erroneously attempts to blow fluid through the device, then this pressure is applied equally to all points in close proximity including the sample collection location; the reservoir vent and the pressure equalisation path. The pressure can be equalised through the pressure equalisation path resulting so that there is no net pressure difference to drive or force the fluid sample through the cartridge too quickly, potentially compromising some aspects of the analysis.

In some embodiments, the size of the reservoir may be sufficient to obviate the need for a vent. Because the reservoir will initially be filled with a gas, normally air, which is inherently compressible, then in embodiments where the reservoir is large in comparison with the analysis zone there may be a sufficient volume of compressible gas that the addition of the sample to the cartridge does not raise the pressure inside the cartridge excessively.

In some embodiments, the lid may be configured to be closed automatically when the cartridge is introduced into a reader or other ancillary device such as a stacker or incubator. The reader may be a device configured to extract data from the cartridge. The reader may be a customer unit deployed within the home or in a central location in a workplace, clinic, in the field or some other location. The reader may be provided with, or associated with, a stacking device so that multiple samples can be received and then held until they are read. The separation between the time of insertion and the time of reading might be due to the reader being busy or the assay being incomplete and therefore further incubation time being required. The provision of automatic closure of the lid when the cartridge enters the reader is beneficial because it provides positive confirmation of the time at which the sample was introduced into the analysis chamber. This information can be used to optimise the reader activity in relation to recording the signal generated.

Alternatively, the reader may be a high throughput device configured to receive data from multiple cartridges and provide a centralised data collection and analysis location.

The invention will now be further and more particularly described, by way of example only, and with reference to the accompanying drawings, in which.

Figure 1:
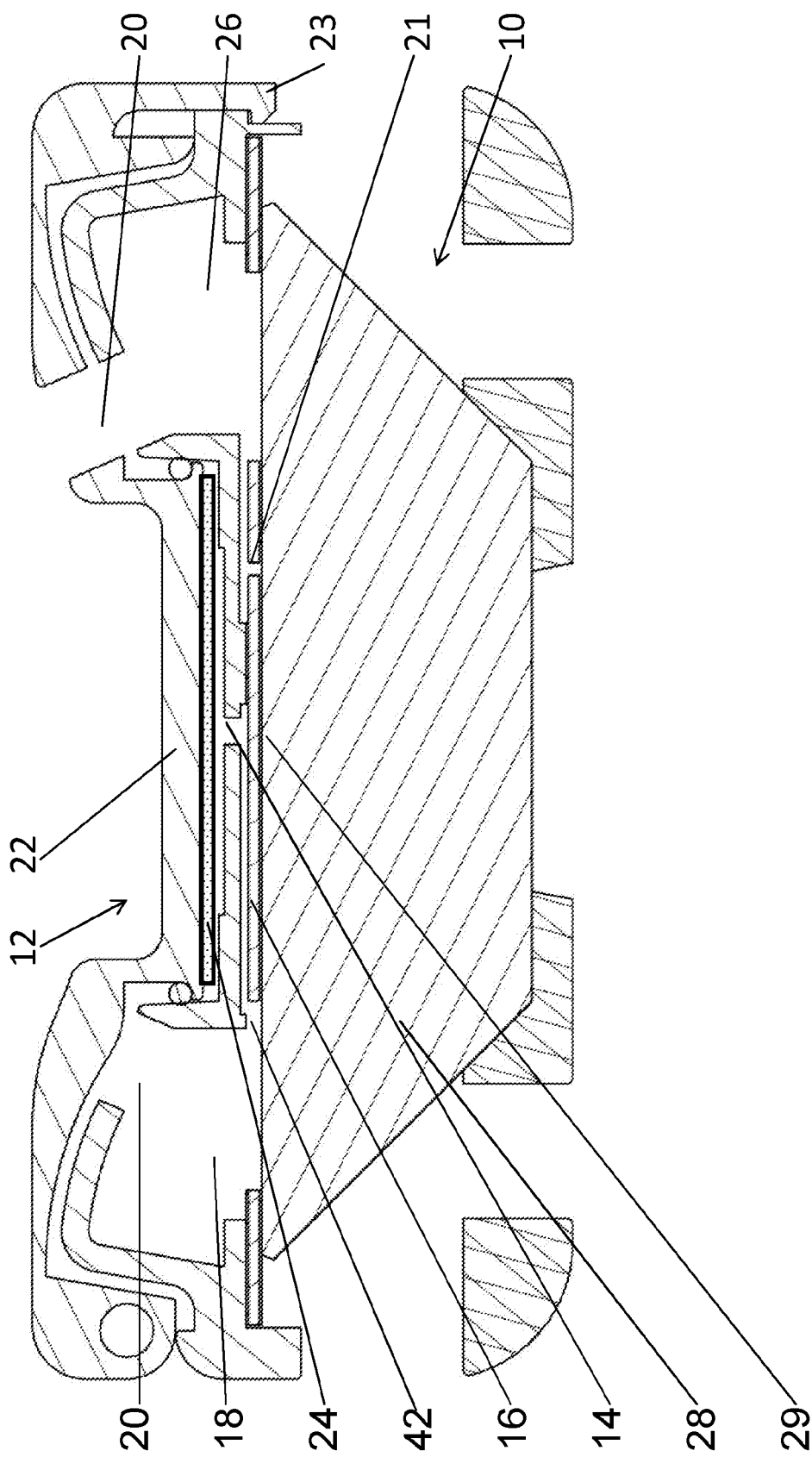
FIG. 1 shows a cross sectional view of cartridge including a sample management module according to the present invention.
Figure 2:
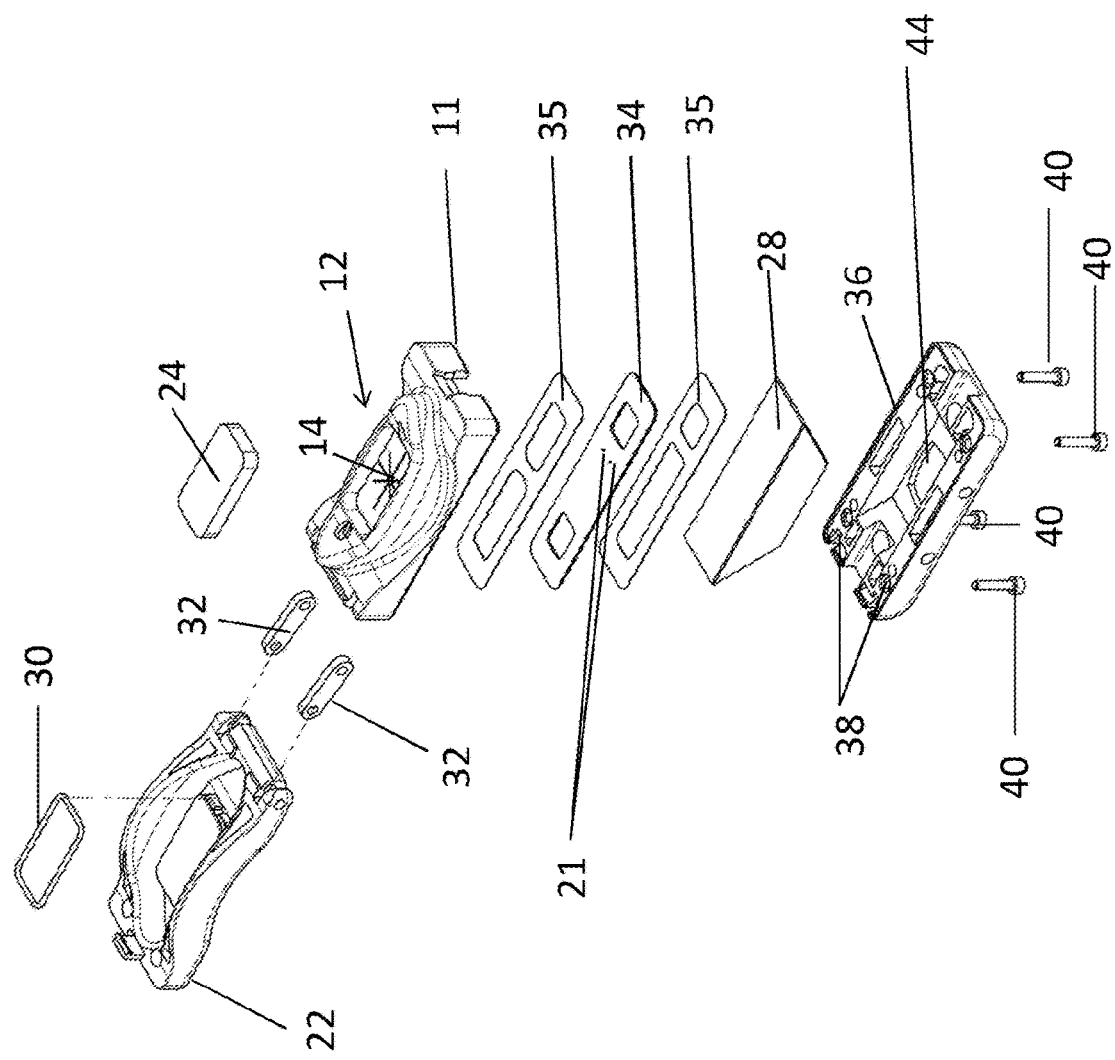
FIG. 2 shows an exploded assembly view of the cartridge showing details of a fluid pathway through the cartridge shown in FIG. 1.

Referring to FIGS. 1 and 2, there is provided a cartridge 10 comprising a sample management module 11 for collecting a fluid sample. The sample is a liquid sample such as a saliva sample. The sample management module 11 comprises a sample collection device 12. The sample collection device 12 comprises a sample collection location 14, a decoupling zone 16 configured to receive a sample from the sample collection device 12, an overflow reservoir 18 in fluid communication with the decoupling zone 16 to accommodate any sample that does not fit into the decoupling zone 16. The overflow reservoir 18 is provided with at least one vent 20 to ensure the pressure within the module 11 can be managed.

The sample management module 11 further comprises a lid 22. The lid is provided with a clip 23. The clip 23 is opening resistant such that, under normal conditions, the user is not easily able to re-open the lid once it has been closed. The lid 22 can be closed via action by the user or by any other means.

The sample collection device 12 further comprises a pad of porous material 24. For example, the pad of porous material may be a sponge 24. A liquid sample such as a saliva sample is excreted onto the pad of porous material 24 directly by spitting and/or drooling. As shown in FIGS. 1 and 2, the pad of porous material 24 can be removable. If the pad is removable, it can be placed in the mouth by the user and saturated with a saliva sample.

The porous material 24 can have a taste to promote salivary excretion in the pad. Additionally or alternatively, the sample collection device 12 has an odour to promote salivary excretion. The porous material 24 may be coated to stop protein absorption on its surface.

The fluid sample can be concentrated by evaporating water whilst the fluid sample is being absorbed and held in the pad of porous material 24. Alternatively, the fluid sample may be further diluted by adding a liquid, such as water into the pad of porous material 24. In order to facilitate dilution, the pad of porous material 24 may be provided pre-moistened. In some examples, not shown in the accompanying drawings, one or more small bust-able bladders may be provided adjacent to the pad of porous material 24. For example, these bladders can be provided on an inner surface of the lid 22 so that, when the lid is closed, the bladder or bladders come into contact with the pad of porous material 24 and bust, allowing their contents to dilute the sample.

The pad of porous material 24 provides a positive indicator such as a change of one or more colours or a change of transparency, in order to provide visible indication when sample has been collected.

The porous material 24 also acts as a filter provided upstream of the decoupling zone 16. The filter is provided to remove or prevent contaminants, cells and unwanted particles from the saliva sample.

In some examples, not shown in the accompanying drawings, a filter may be provided in the form of a semi-permeable layer. This provides a base for the sample management module and holds the fluid sample as it is provided. Once the sample is held on the layer, the lid is closed, providing sufficient pressure to force the sample through the semi-permeable layer. This layer will filter out any particles that exceed a pre-determined threshold size. The layer may be cellulose acetate, a polypropylene mesh or any other suitable semi-permeable layer. In some examples, the semi-permeable layer is provided in place of the pad of porous material. In some examples both the semi-permeable layer and the pad of porous material are included.

The porous material 24 absorbs the sample and holds the sample in the sample collection device 12 until the lid 22 is closed and the sample is forced from the porous material 24 out of the sample collection location 14 and into the decoupling zone 16. The saliva sample enters into the decoupling zone where an overflow reservoir 18 is in fluid communication with the decoupling zone 16.

The decoupling zone 16 is positioned or located near to the overflow reservoir 18 so that the decoupling zone 16 can be in fluid communication with the overflow reservoir 18.

As illustrated in FIG. 1, the overflow reservoir 18 may be used to accommodate any sample that does not fit into the decoupling zone 16. The overflow reservoir 18 is provided with one or more vents 20. The vent 20 is used to ensure that the pressure within the sample management module 11 can be managed. For example, the overflow reservoir 18 provided with the vent 20 is used to enable air to escape. This is to ensure that positive pressure cannot build up within the overflow reservoir 18.

Figure 3:
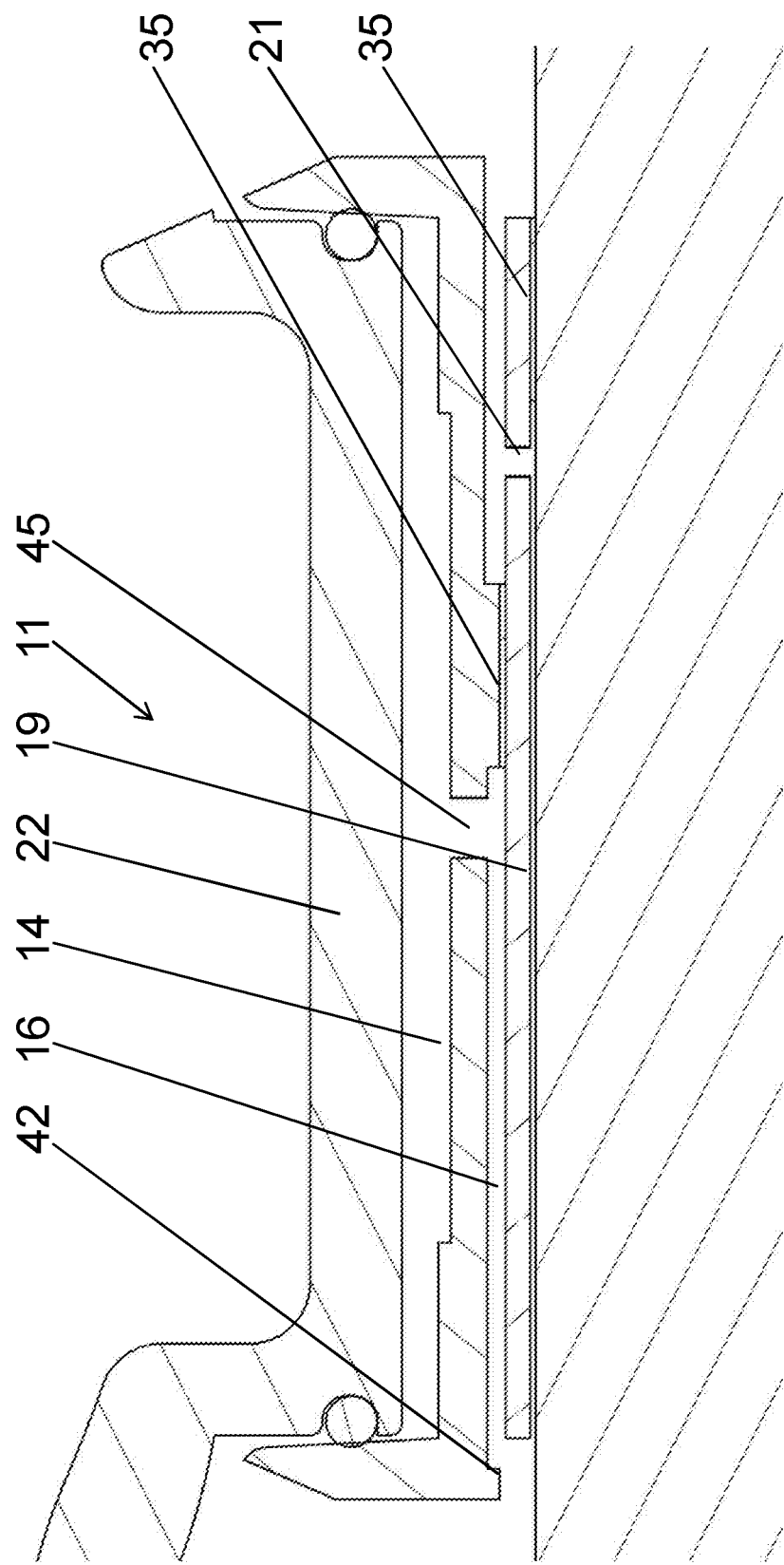
FIG. 3 shows the detail of the fluid pathway provided through the sample management module that forms part of the cartridge of FIG. 1.

Referring to FIGS. 1 and 3, there is illustrated a cross section through the cartridge 10 focussing on the area in the immediate vicinity of the sample management module 11. Once the sample has been collected in the sample management module 11 it can be flowed into the analysis zone 19 for analysis. The flow of the fluid can be actively or passively controlled. In the example shown in FIG. 3, the flow is instigated by the closing of the lid 22, which forces the sample to move from the sample collection location 14 into the decoupling zone 16. From the decoupling zone 16 the sample moves into the analysis zone 19 by capillary forces. A lip 42 is provided to guide the fluid flow from the decoupling zone 16 into the analysis zone 19. The lip 42 ensures that the sample does not bypass the analysis zone 19 and move directly into the overflow reservoir 18. In order to flow to the analysis zone 19, the sample flows through the decoupling zone 16. Once the analysis zone 19 is full any additional sample will flow into the overflow reservoir 18 and the gas displaced will exit via the vent 20.

In the example shown in FIG. 3 the lid 22 is provided with an annular depression 41 in which is seated an O-ring 30. The O-ring 30 provides a fluid seal when the lid 22 is closed. The O-ring 30 prevents fluid from leaving the sample collection location in any direction other than that which is intended, namely moving into the decoupling zone 16 and then into the analysis zone 19. Ensuring that liquid sample cannot escape from the sample management module 11 is important for both quality assurance for the user and also contamination risk management for the reader into which the cartridge is introduced.

The cartridge 10 further comprises a pressure equalisation path 26 from the analysis zone 19 back through the sample management module 11. This is provided in the illustrated embodiment of FIG. 1 to include an additional vent 20 that ensures that there is a closed loop for air recirculation.

Furthermore, the analysis zone 19 comprises a substrate 29. The substrate 29 is the upper surface of optical element 28. It will be understood that, in this context "upper" refers merely to the illustrated configuration as displayed on the accompanying drawings. It should not be construed to limit the use of the cartridge 10 to this configuration. In use, the cartridge 10 may be held in any orientation without limitation.

The optical element 28 made from glass or polymer. The optical element 28 illustrated in FIG. 1 is a single prism shaped optical element. However, in other examples not shown in the accompanying drawings, a different format of optical element could be deployed. The optical element 28 may include a plurality of separate individual elements configured to operate together as the optical element. The geometry may be prismatic as illustrated in FIG. 1, but it could also be a wave guide. Furthermore, in other embodiments not shown in the accompanying drawings, the substrate 29 may be a separate entity from the optical element 28. In these embodiments, the substrate could be a glass coverslip or similar element that is provided adjacent to the optical element 28. In embodiments where a separate substrate 29 is provided the interface between the substrate 29 and the optical element may be provided with index matching fluid in the form of a liquid or gel.

In FIG. 1 a prism shaped optical element 28 providing the substrate 29. In other examples, not shown in the accompanying drawings, the optical element may be a triangular- or a cuboid-optical element. In addition, a plurality of capture components is deposited onto the substrate 29. In order to control the flow of the sample into the analysis zone 19, a vent hole 21 is provided adjacent the surface of the optical element 28. The vent hole 21 enables the air, or inert gas, contained within the cartridge prior to the introduction of the sample, to exit the cartridge 10 as the sample is introduced. This prevents a build-up of pressure within the cartridge 10 when the sample moves into the analysis zone 19.

The vent hole 21 is sized such that the surface tension of the liquid sample prevents the sample from moving through the vent hole 21. As a result, the vent hole acts as a constriction in the flow path that causes the bulk movement of the sample to slow considerably or even for bulk movement to stop completely once the sample has filled the analysis zone 19. As a result, the only bulk movement during the incubation time arises from evaporation at the vent hole 21.

The cartridge 10 can be inserted into a reader for measurement. The measurement taken by the reader may be an optical measurement, such as light scattering or fluorescence measurements. The excitation light may be provided in the form of total internal reflection (TIR) at the substrate 29. The reader may be a device configured to extract data from the cartridge. For example, the reader may be able to extract data associated with certain diseases or symptoms from the saliva sample.

FIG. 2 provides an exploded view of a cartridge 10 set up according to the present invention. The cartridge 10 comprises the sample management module 11, a sample collection device 12 comprising a pad of porous material 24 such as a sponge. The body of the sample management module 11 is shaped to provide a mouthpiece that conveniently accommodates the user's lips when providing a saliva sample into the sample collection location 14. The edge of the mouthpiece can be impregnated with a pleasant taste which may help the user to provide a saliva sample. The pad 12 of porous material can be adhered to the sample collection location 14. Alternatively, the porous pad can be removable from the sample management module 11. An O-ring 30 can be provided on top of the sample collection device 12 in order to create a seal when the lid 22 is closed on top of the sample collection device 12. Hinges 32 can be provided at the ends of the sample management module 11. The lid 22 may be provided with one or more hinges 32 so that the lid can be joined to the sample management module 11. The cartridge may further comprise an additional layer 34 between the substrate 28 and the sample management module 11. This intermediary layer 34 is provided with two vents 21 symmetrically placed either side of the centre line. This intermediary layer 34 is optional and is intended to mitigate against inaccuracies in the shape of the sample management module 11, caused by the manufacture methodology deployed. Depending on the method of manufacture chosen, this layer may be redundant. One or more gaskets 35 are provided on top of the optical element 28. There is provided a slot within the gasket 35 which forms the decoupling zone 16 and the analysis zone 19. The example shown in FIG. 3 has two gaskets 35. The first ensures that the sample moves correctly into the decoupling zone when it leaves the sample collection location 14. Once the fluid flows through the orifice 45 that links the sample collection location 14 to the decoupling zone, the gasket 35 ensures that, on emerging from the orifice 45, the only route that the fluid can take is into the decoupling zone 16. The gasket 35 blocks off the alternative, incorrect flow direction. The second gasket 35 is provided beyond the vent 21 adjacent the upper surface of the optical element 28. This gasket 35 forms part of the walls of the analysis zone 19 and thereby prevents fluid from leaving the analysis zone 19 and, potentially exiting the cartridge 10.

As shown in FIG. 2, the optical element 28 can sit within a holder 36. The holder comprises one or more holes 38 for screws 40. The holder 36 also includes a viewing aperture 44 through which the transmitted light can be observed. The optical element 28 can be fixed within the holder 36 by one or more screws 40. As an example only, the screw 40 can be a head socket head cap screw M1.6 stainless steel black oxide.

Figure 4A:
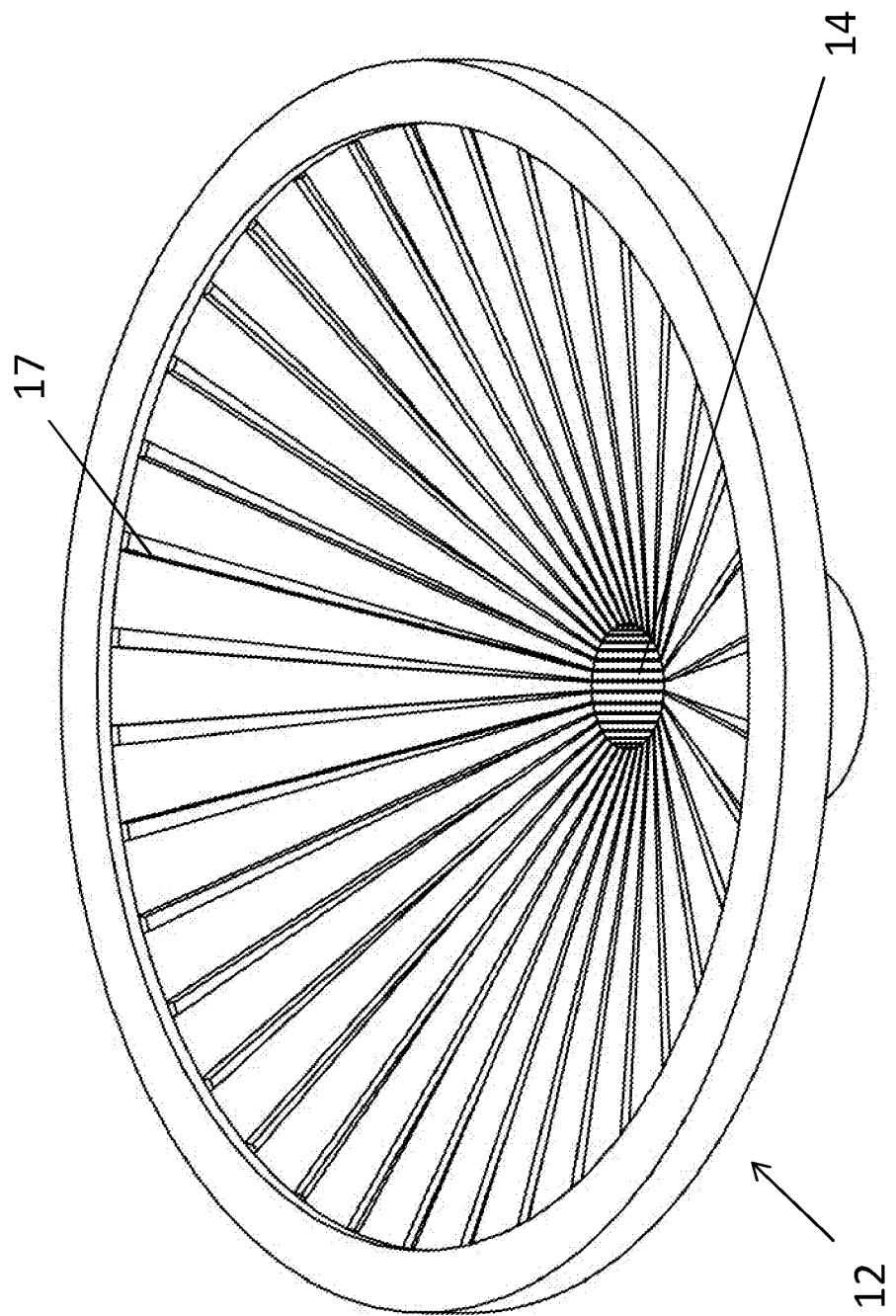
FIGS. 4A to 4C show an alternative example of a sample collection device according to the present invention.
Figure 4B:
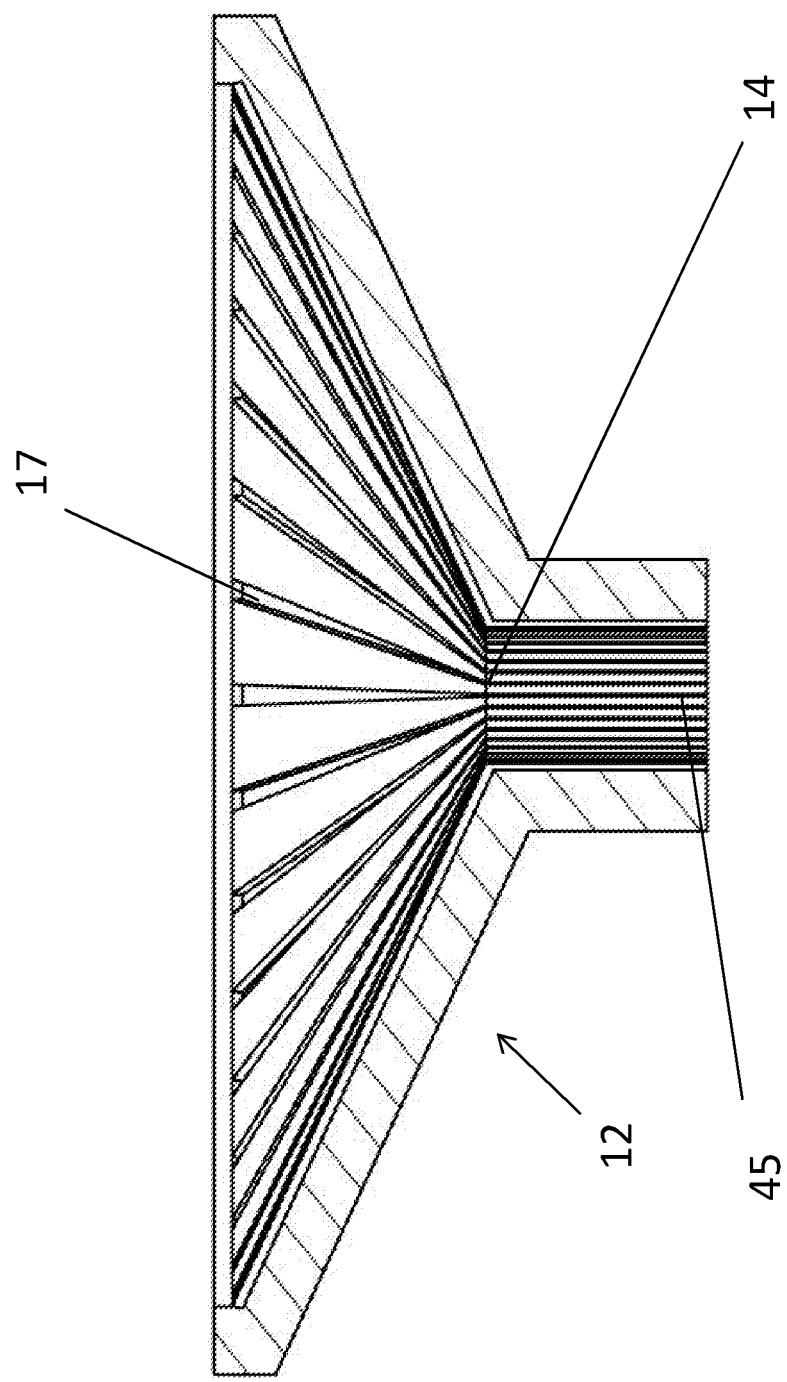
Figure 4C:
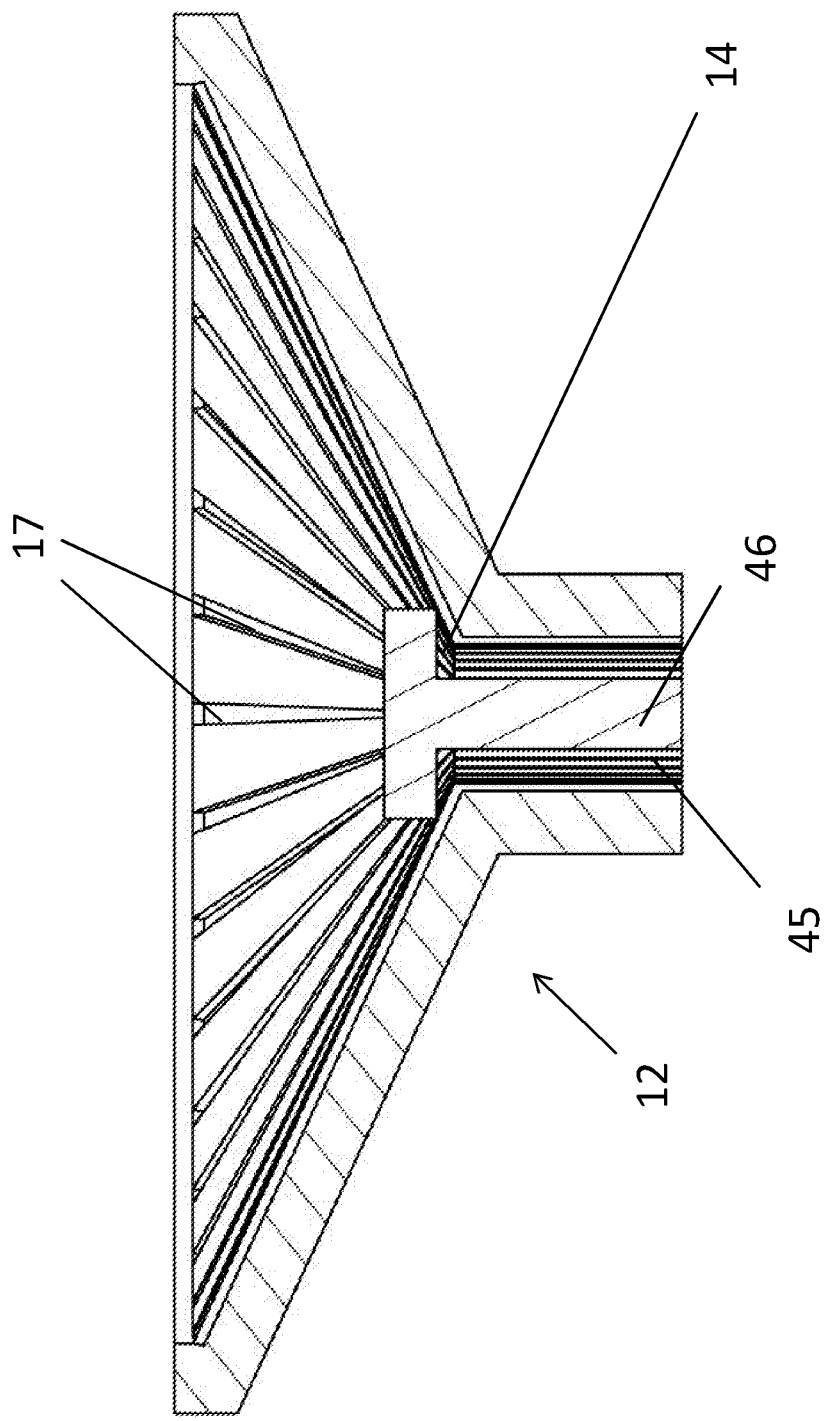

An alternative embodiment of the sample collection device 12 is shown in FIG. 4. The sample collection device 12 is configured to enable the sample to be drawn passively into the decoupling zone 16. This obviates the need for a lid to force the sample into the cartridge 10. Grooves 17 are provided to enable the sample to be drawn passively into the decoupling zone 16. The grooves 17 enable the sample to move via capillary action from the sample collection device 12 into the decoupling zone 16. In some embodiments, the grooves 17 can be hydrophilic. The grooves 17 can be injection moulded into the plastic receptacle, machined, laser cut or stamped or chemically etched. In the embodiment illustrated in FIG. 4C, an additional lid 46 is provided that is configured to block the orifice so that the only route into the decoupling zone 16 is via the grooves 17. As a result of this restriction, the grooves 17 act as a form of filter because any particle too large to enter the groove would not be able to move into the decoupling zone 16.

FIGS. 5 to 8 show further embodiments that optimise the pressure management within the cartridge through a flow control system including at least a vent 20, having resistance R1 and a vent hole 21 having resistance R2. The flow control system is configured to reduce the bulk flow movement of the sample once the sample reaches the analysis zone 19.

The flow control system may be required to slow the bulk movement of the sample sufficiently so that movement of fluids within the analysis zone 19 is dominated by diffusion.

The flow control system may effectively halt the bulk fluid flow. Alternatively, the bulk fluid flow may be reduced to 1 mm/minute, 0.5 mm/minute, 0.25 mm/minute or even substantially 0.0 mm/minute, i.e. stationary, so that the diffusion of the components within the sample is significant.

The flow control system may be provided distally of the analysis zone 19. By placing the flow control system distally, or downstream, of the analysis zone 19, the flow of sample into the fluid pathway 16 is unimpeded thereby enabling the sample to be quickly introduced into the cartridge. The flow control system then acts to slow the flow of the sample once it has reached the analysis zone 19.

The flow control system can take any form that is effective in slowing the flow. The flow controller may include a capillary stop or a narrow or tortuous path. Each of the examples shown in FIGS. 5 to 8 includes a vent, or air vent 20 with resistance R1. This vent 20 is provided on the reservoir 18 to manage the pressure in the reservoir 18 by enabling air to leave the reservoir 18 as the sample is introduced into the cartridge. The vent 20 may be a simple opening or may include a membrane.

The flow control system also includes a vent hole 21 with resistance R2. The vent hole 21 is positioned at the exit of the analysis zone 19. The vent hole 21 may include a porous pad. The vent hole 21 may be a capillary stop.

The vent hole 21 and vent 20 are selected such that R2>R1. This selection of resistances ensures that once the analysis zone has been filled any additional sample fluid flows into the reservoir 18.

Figure 5:
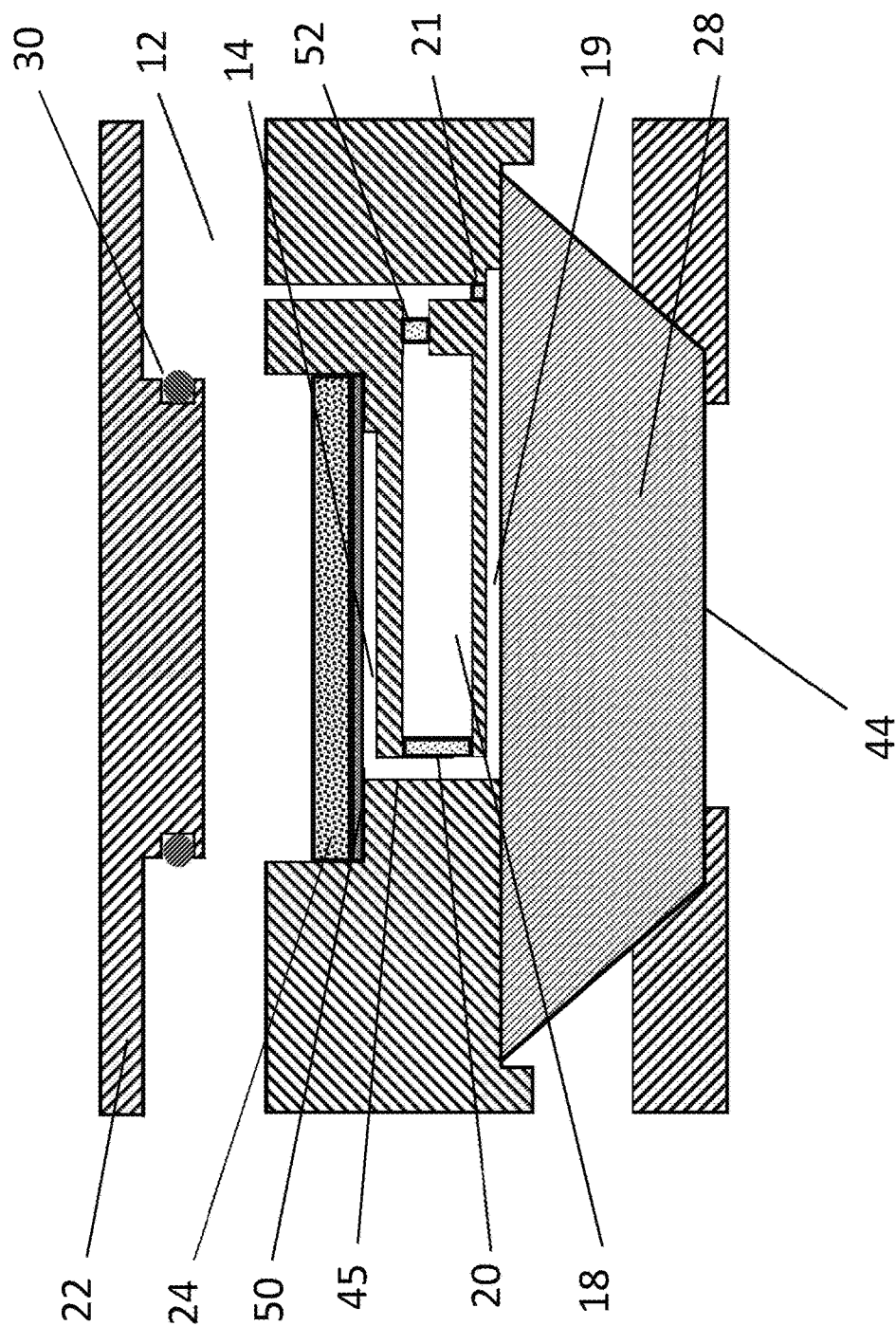
FIG. 5 shows a cross sectional view of a cartridge that is configured for an active, or rapid, initial fill.

As shown in FIG. 5, the flow control system may further comprise an additional flow control element 52 which is provided at the exit to the reservoir 18.

The example shown in FIG. 5 may be termed an active fill configuration because instead of passively drawing or sucking the sample into the analysis zone 19 by capillary action, positive pressure is instead provided by the closure of the lid 22. This creates a rapid fill of the analysis zone 19 on the closure of the lid 22. This flow is then managed and reduced by the flow control system which ensures that the analysis zone is preferentially filled and then, once full, any additional sample is flowed into reservoir 18.

Figure 6:
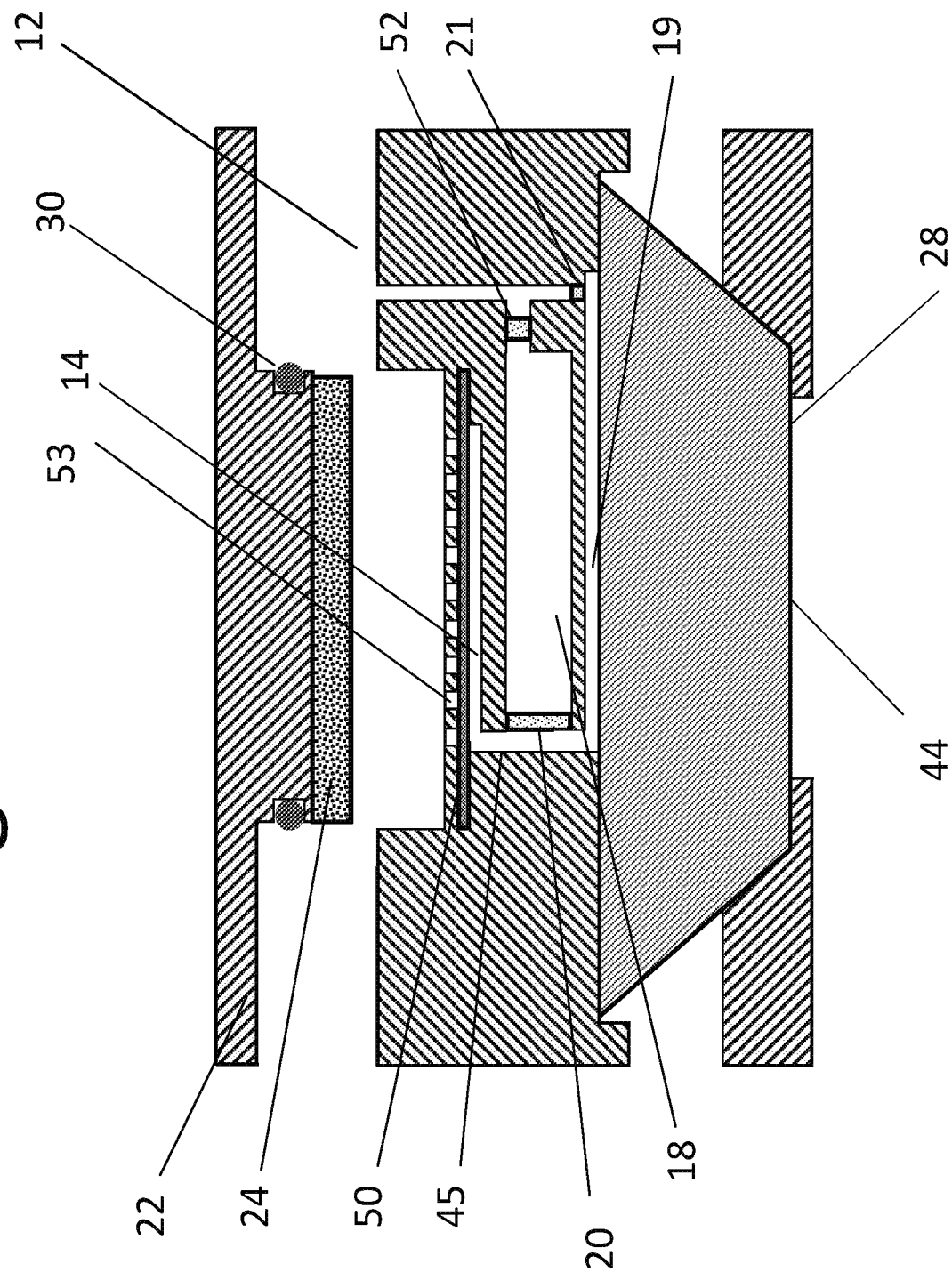
FIG. 6 shows a cross sectional view of a cartridge that is provided with a removable collection area.

FIG. 6 shows an example in which the sample collection device 12 is removable. In this example, the sample collection device 12 is incorporated into the lid 22. In the illustrated example, the pad 24 is also provided on the removable lid 22. However, the presence of the pad 24 is not essential to this configuration as the filtration functionality of the pad 24 can be provided elsewhere within the cartridge. For example, a separate filter 50 can be provided in the cartridge so that the sample is filtered once the lid 22 is closed and the sample is introduced. Additionally, or alternatively, there may be provided a protective layer 53 over top of the separate filter 50. The provision of the filter 50 within the cartridge or the provision of the protective layer 53 to provide separation both protect the it from accidental damage by the user. The protective layer 53 illustrated in FIG. 6 takes the form of a very coarse grain filter with large entry holes. In other embodiments, not illustrated, the protective layer could be a semi permeable membrane or just a single large entry hole.

Figure 7:
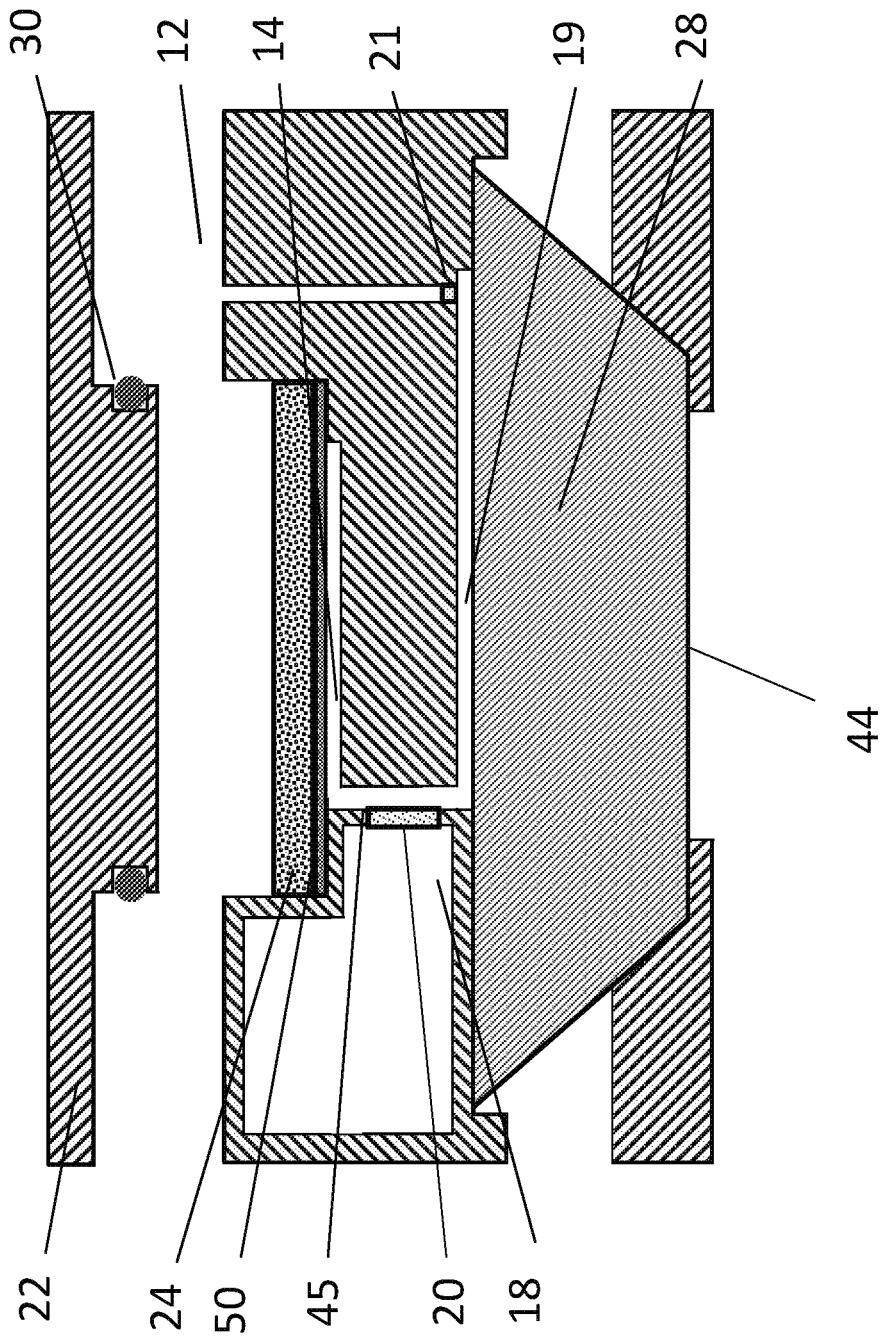
FIG. 7 shows a cross sectional view of a cartridge that is provided with a large reservoir.

Although not optimised for use by an unskilled operative and therefore less appropriate for a point of care scenario, it is possible to implement the configuration illustrated in FIG. 7. The illustrated embodiment shows a large reservoir 18 that can accommodate a reasonable sample overflow, i.e. the part of the sample remaining once the analysis zone 19 is filled, without a substantial increase in pressure arising from the compression of the gas within the reservoir. This example may be better suited to fluid samples that are not saliva samples provided directly from the mouth. For example, if the sample is pipetted into the cartridge, this example may be effective.

Figure 8:
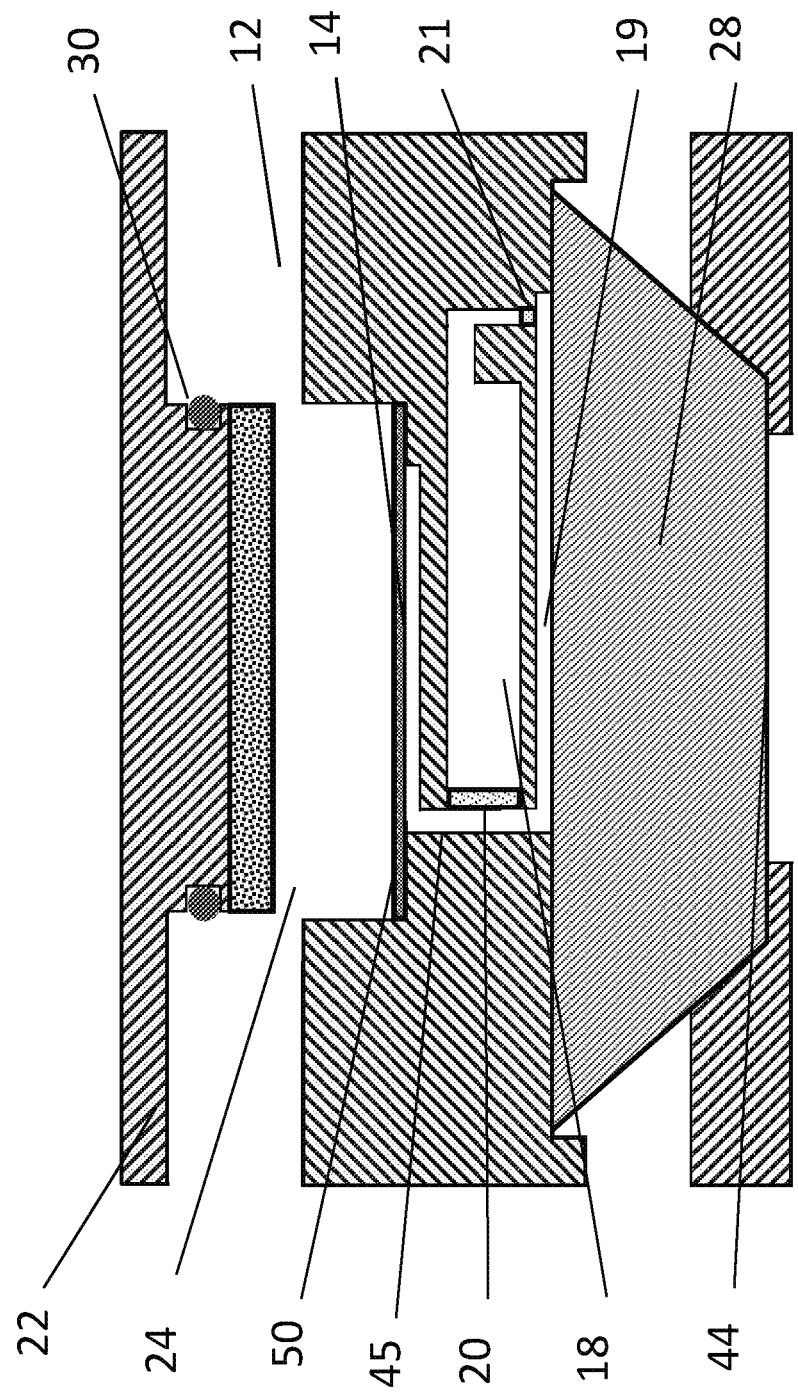
FIG. 8 shows a cross sectional view of a cartridge that is fully enclosed.

FIG. 8 shows a configuration in which the reservoir 18 is connected to the vent hole 21. Therefore, no flow control element 52 is provided and the vent hole 21 does not connect to ambient. In this configuration, the management of pressure must be completed entirely within the cartridge and this is achieved by connection the analysis zone 19 to the reservoir 18. Due to the small cross sectional area of the analysis zone 19 in comparison with the reservoir 18, the capillary forces will ensure that the analysis zone 19 fills preferentially over the reservoir 18.

Various further aspects and embodiments of the present invention will be apparent to those skilled in the art in view of the present disclosure.

"and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

Unless context dictates otherwise, the descriptions and definitions of the features set out above are not limited to any particular aspect or embodiment of the invention and apply equally to all aspects and embodiments which are described.

It will further be appreciated by those skilled in the art that although the invention has been described by way of example with reference to several embodiments. It is not limited to the disclosed embodiments and that alternative embodiments could be constructed without departing from the scope of the invention as defined in the appended claims.

The invention claimed is:

1. A cartridge comprising a sample management module for collecting a fluid sample, the module comprising:
   a sample collection device comprising a sample collection location and a filter;
   a decoupling zone configured to receive sample from the collection device;
   an overflow reservoir in fluid communication with the decoupling zone to accommodate any sample that does not fit into the decoupling zone; and
   an optical element comprising a surface with a plurality of capture components deposited thereon,
   wherein the overflow reservoir is provided with a vent to ensure pressure within the module can be managed,
   wherein the cartridge further comprises an analysis zone downstream of the sample management module and a vent hole downstream of the analysis zone,
   wherein the vent hole is configured to enable air or inert gas to exit the cartridge, and
   wherein the analysis zone comprises the capture component deposited surface of the optical element.

2. The cartridge according to claim 1, wherein the filter is a pad of porous material.

3. The cartridge according to claim 2, wherein the pad of porous material is passivated.

4. The cartridge according to claim 2, wherein the pad of porous material is configured to provide visible indication when sample has been collected.

5. The cartridge according to claim 4, wherein positive indication is one or more of a colour change or a transparency change.

6. The cartridge according to claim 2, wherein the pad is provided with a taste to promote salivary excretion.

7. The cartridge according to claim 2, wherein the porous material is provided upstream of the decoupling zone.

8. The cartridge according to claim 1, further comprising a lid.

9. The cartridge according to claim 8, wherein the lid is configured such that the closure of the lid forces the sample from the sample collection location into the decoupling zone.

10. The cartridge according to claim 2, wherein the sample collection device and pad are removable.

11. The cartridge according to claim 7, wherein the lid compresses the pad to squeeze the sample out of the pad and into the decoupling zone.

12. The cartridge according to claim 1, wherein the optical element is configured to enable analysis by TIR.

13. The cartridge according to claim 1, further comprising a pressure equalization path.

14. The cartridge according to claim 8, wherein the lid is configured to be closed automatically when the cartridge is introduced into a reader or ancillary device.

* * * * *